(12) United States Patent
Moissl et al.

(10) Patent No.: US 8,512,271 B2
(45) Date of Patent: Aug. 20, 2013

(54) DEVICE AND METHOD FOR DETERMINING A DIALYSIS FLUID FLOW RATE FOR EXTRACORPOREAL BLOOD TREATMENT

(75) Inventors: Ulrich Moissl, Bad Vilbel (DE); Andreas Wüpper, Büttelborn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1002 days.

(21) Appl. No.: 12/443,001

(22) PCT Filed: Sep. 25, 2007

(86) PCT No.: PCT/EP2007/008297
§ 371 (c)(1),
(2), (4) Date: Mar. 26, 2009

(87) PCT Pub. No.: WO2008/037410
PCT Pub. Date: Apr. 3, 2008

(65) Prior Publication Data
US 2010/0042035 A1      Feb. 18, 2010

(30) Foreign Application Priority Data
Sep. 26, 2006   (DE) .......................... 10 2006 045 437

(51) Int. Cl.
*A61M 37/00*    (2006.01)
*B01D 63/00*    (2006.01)
*C02F 1/44*     (2006.01)
*C02F 11/00*    (2006.01)

(52) U.S. Cl.
USPC ...................... 604/6.11; 210/321.71; 210/647

(58) Field of Classification Search
USPC .... 604/4.01–6.14, 19–22, 29–31; 210/321.7, 210/645–647; 422/44–48; 128/898
See application file for complete search history.

(56) References Cited

U.S. PATENT DOCUMENTS 5,092,836 A * 3/1992 Polaschegg .................. 604/6.11
5,100,554 A   3/1992 Polaschegg
(Continued)

FOREIGN PATENT DOCUMENTS

DE      39 09 967 A1    9/1990
DE      197 39 100 C1   2/1999
(Continued)

OTHER PUBLICATIONS

International Search Report, PCT/EP2007/008297, mailed Jan. 24, 2008.

(Continued)

*Primary Examiner* — Philip R Wiest
(74) *Attorney, Agent, or Firm* — Kenyon & Kenyon LLP

(57) ABSTRACT

The present invention relates to a device and to a method for determining the dialysis fluid flow rate for an extracorporeal blood treatment device. The dialysis fluid flow rate $Q_d$ is determined in accordance with the blood flow rate $Q_b$ or the blood flow rate $Q_b$ is determined in accordance with the dialysis fluid flow rate $Q_d$, wherein by increasing about a specific value, the increase of a variable characterising the efficiency of the blood treatment, in particular clearance K, does not exceed the specific value. The present invention also relates to a blood treatment device comprising a device for determining the dialysis fluid flow rate or blood flow rate and to a method for operating an extracorporeal blood treatment device. As a result, an optimal dialysis fluid flow rate and/or blood flow rate calculates the requirement in accordance with a high efficiency of the dialysis treatment and in accordance with a reduced consumption of the dialysis liquid.

18 Claims, 5 Drawing Sheets

(56) References Cited

U.S. PATENT DOCUMENTS

| | | | |
|---|---|---|---|
| 5,110,477 A | 5/1992 | Howard et al. | |
| 5,507,723 A * | 4/1996 | Keshaviah | 604/6.11 |
| 6,217,539 B1 | 4/2001 | Goldau | |
| 7,172,569 B2 * | 2/2007 | Kleinekofort | 604/6.06 |

FOREIGN PATENT DOCUMENTS

| | | |
|---|---|---|
| DE | 197 46 367 C2 | 8/1999 |
| DE | 69531137 T2 | 4/2004 |
| EP | 0389840 A | 10/1990 |
| WO | 95/32010 A1 | 11/1995 |

OTHER PUBLICATIONS

Sigdell et al., "Clearance of a Dialyzer Under Varying Operation Conditions," Artificial Organs 10(3):219-225, 1986.

International Preliminary Report on Patentability, PCT/EP2007/008297, mailed Apr. 16, 2009.

* cited by examiner

DEVICE AND METHOD FOR DETERMINING A DIALYSIS FLUID FLOW RATE FOR EXTRACORPOREAL BLOOD TREATMENT

CROSS REFERENCE TO RELATED APPLICATIONS

This is a 371 national phase application of PCT/EP2007/008297 filed Sep. 25, 2007, claiming priority to German Patent Application No. 10 2006 045 437.5 filed Sep. 26, 2006.

FIELD OF INVENTION

The present invention relates to a system and method for presetting a dialysis-fluid flow rate or blood flow rate for an extracorporeal blood-treating apparatus which has a dialyser which is divided by a semi-permeable membrane into a blood chamber through which blood flows at a preset blood flow rate and a dialysis-fluid chamber through which dialysis fluid flows at a preset dialysis-fluid flow rate. The present invention also relates to a blood-treating apparatus having an arrangement for presetting a dialysis-fluid flow rate or blood flow rate and to a method of operating an extracorporeal blood-treating apparatus.

BACKGROUND OF THE INVENTION

In processes used in blood cleansing therapy such as hemodialysis, hemofiltration and hemodiafiltration, blood from a patient is conveyed through an extracorporeal blood circuit in which there is a dialyser or filter, which is divided by a semi-permeable membrane into a blood chamber and a dialysis-fluid chamber or filtrate chamber. In hemodiafiltration, both hemodialysis and hemofiltration are performed. The present invention relates to all processes used in blood cleansing therapy in which blood flows through the blood chamber of a dialyser and dialysis fluids flows through the dialysis-fluid chamber.

There are various known physical and/or chemical metrics by means of which the performance of the dialyser and/or the effectiveness of a dialysis treatment can be specified. One known metric for the performance of a dialyser is the clearance K. The clearance K of a substance is that proportion of the total flow through the dialyser which is totally cleared of the substance concerned. For the effectiveness of a dialysis treatment, what is of crucial significance is what is termed the dialysis dose (Kt)/V, which is defined as the quotient of the product of clearance K for urea multiplied by effective treatment time t, divided by the volume V of the patient's body through which urea is distributed.

U.S. Pat. No. 5,100,554 describes a method of determining clearance in which dialyser electrolyte transfer is measured at each of two different dialysate input concentrations. It is known from U.S. Pat. No. 5,100,554 that the effectiveness of dialysis treatment is dependent on the blood flow and the dialysis-fluid flow.

DE 695 31 137 T2 (WO 95/32010) describes a method and arrangement for optimising the effectiveness of a dialysis treatment, in which a metric characteristic of the effectiveness of the dialysis treatment is measured during the treatment and a parameter of the dialysis treatment is determined on the basis of the metric to allow optimum effectiveness to be obtained for the dialysis treatment. It can be deduced in detail from the publication that a processor increases the selected parameters, for example the blood flow rate, in a stepwise manner in defined increments, a urea sensor continuously measuring a characteristic variable, in that a sample of the draining-off dialysate is taken. By comparing the currently measured concentration with the preceding concentration, it is ascertained whether the current concentration is smaller or greater than the preceding concentration. If the current concentration is smaller than the preceding concentration, it is concluded that the preceding concentration represents the optimum value. As a result, the maximum value of the concentration is intended to be determined.

In the past, known pieces of dialysis apparatus have been operated with a constant flow of dialysis fluid which could not be altered by the user. More recent pieces of apparatus on the other hand allow different dialysis-fluid flow rates, such for example as 300, 500 and 800 ml/min, to be set manually. To achieve a high clearance, quite high dialysis-fluid flows at quite high blood flows are required.

When a given dialysis-fluid flow is being set, although high clearance can be obtained with a high dialysis-fluid flow, the costs of supplying fresh dialysis fluid and of disposing used dialysis fluid go up. What is therefore desired in practice is relatively high clearance for a relatively low consumption of dialysis fluid.

It is known that, if the widely employed dialysers are used at a ratio of blood flow to dialysis-fluid flow of 1:2, only a slight reduction in clearance occurs in comparison with a non-variable dialysis-fluid flow of 500 ml/min (J. E. Siegdell, B. Tersteegen, *Artificial Organs*, 10(3), pages 219-225, 1986).

U.S. Pat. No. 5,092,836 therefore proposes controlling dialysis-fluid flow as a function of blood flow in accordance with preset criteria. In particular, what is proposed is for a dialysis-fluid flow to be set that is obtained by multiplying the blood flow by a constant factor. As well as a linear relationship between blood flow and dialysis-fluid flow, what is also proposed is a numerical data matrix, which, for each blood flow of a given dialyser, gives that dialysis-fluid flow at which a given percentage is achieved of the maximum clearance that would have to exist if the dialysis-fluid flow were assumed to be infinitely high. In practice, the percentage may be, for example, 95%.

SUMMARY OF THE INVENTION

One object of the present invention is to specify a system and method for presetting an optimum dialysis-fluid flow rate or blood flow rate for an extracorporeal blood-treating apparatus in which account is taken of the demand for high effectiveness on the part of the dialysis treatment and of the demand for low consumption of the dialysis fluid. A further object of the present invention is to provide a blood-treating apparatus with which a dialysis treatment of relatively high effectiveness can be performed at a relatively low dialysis-fluid flow. It is also an object of the present invention to specify a method of operating a blood-treating apparatus to enable a dialysis treatment of relatively high effectiveness to be performed with a reasonable consumption of dialysis fluid.

In the system according to the present invention and the method according to the present invention for presetting a dialysis-fluid flow rate or blood flow rate for an extracorporeal blood-treating apparatus, that dialysis-fluid flow rate $Q_d$ is determined, for a preset blood flow rate, which, if it were increased by a given amount, would result in a metric characteristic of the effectiveness of the blood treatment increasing by not less than a given amount. Alternatively, that blood flow rate $Q_b$ may also determined, for a preset dialysis-fluid flow rate, which, if it were increased by a given amount, would result in a metric characteristic of the effectiveness of the blood treatment increasing by not less than a given amount.

The system according to the present invention and the method according to the present invention assume in this case that, although, as from an optimum value for the dialysis-fluid flow rate at a preset blood flow rate, or for the blood flow rate at a preset dialysis-fluid flow rate, an increase in the effectiveness of the dialysis treatment can still by achieved by a further increase in the dialysis-fluid flow rate and the blood flow rate in the respective cases, the additional dialysis fluid and the further increase in the blood flow which is required in the respective cases for such treatment of greater effectiveness does not bear an economical relationship to the increase in effectiveness which it gives. What is therefore aimed for as a target criterion is that operating point at which the consumption of additional dialysis fluid which would be needed to increase clearance by a given amount does not exceed a given amount, i.e. it is determined how many ml/min of dialysis fluid one is prepared to consume to achieve a further ml/min of clearance. Alternatively, what is aimed for is that operating point at which a further increase in the blood flow rate which would be necessary to increase clearance by a given amount does not exceed a given amount.

Different modes of treatment in which the effectiveness of the blood treatment differs can be preset, in which case that dialysis-fluid flow rate $Q_d$ or blood flow rate $Q_b$ is determined for the given mode of treatment which, if it were increased by a given amount, would result in the metric characteristic of the effectiveness of the blood treatment increasing by not less than an amount that is assigned to the given mode of treatment.

In practice, a ratio of 10:1 for the quotient $Q_d/K$ of dialysis-fluid flow rate $Q_d$ divided by clearance K, has proved satisfactory. Basically, however, a ratio covering a range from 5:1 to 20:1 is also acceptable.

The optimum dialysis-fluid flow rate $Q_{dopt}$ or blood flow rate $Q_{bopt}$ is dependent not only on the blood flow rate and dialysis-fluid flow rate respectively but also on the dialyser that is used for the dialysis treatment. The system according to the present invention and the method according to the present invention therefore make provision for the optimum dialysis-fluid flow rate or blood flow rate, as the case may be, to be determined as a function of a metric characteristic of the dialyser, and in particular the mass transfer coefficient k0A of the dialyser.

The optimum dialysis-fluid flow rate $Q_{dopt}$ as a function of the blood flow rate $Q_b$ and of a metric characteristic of the dialyser, and particularly the mass transfer coefficient k0A, can be stored in a memory of the dialysis apparatus as a three-dimensional family of characteristics. However, for reasons of storage space, the family of characteristics is preferably defined by a suitable mathematical equation from which the optimum dialysis-fluid flow rate can be calculated for preset blood flow rates and mass transfer coefficients. The three-dimensional family of characteristics is preferably approximated by a higher-order polynomial, and particularly a third-order polynomial in two or more variables including all the cross-terms. The same is true, mutatis mutandis, of the alternative of an optimum blood flow rate as a function of the dialysis-fluid flow rate.

For the calculation of the optimum dialysis-fluid flow rate or blood flow rate, the system according to the present invention preferably has a calculating unit by which the optimum dialysis-fluid flow rate is calculated as a function of the blood flow rate, or vice versa, for a given dialyser or for different dialysers having different mass transfer coefficients.

The system according to the present invention and the method according to the present invention for presetting a dialysis-fluid flow rate or a blood flow rate may be used to make a suggestion to the treating physician for the setting of an optimum dialysis-fluid flow rate or blood flow rate. The system according to the present invention may be part of a blood-treating apparatus in this case or may form a separate unit. The blood-treating apparatus will however preferably already have the system according to the present invention for presetting the optimum dialysis-fluid flow rate or blood flow rate. It is also preferable for the preset dialysis-fluid flow rate or blood flow rate not just to be suggested to the treating physician but also to be set automatically for the blood treatment.

BRIEF DESCRIPTION OF THE DRAWINGS

An embodiment of the present invention is explained in detail below by reference to the drawings. In the drawings.

DETAILED DESCRIPTION OF THE DRAWINGS

Figure 1:
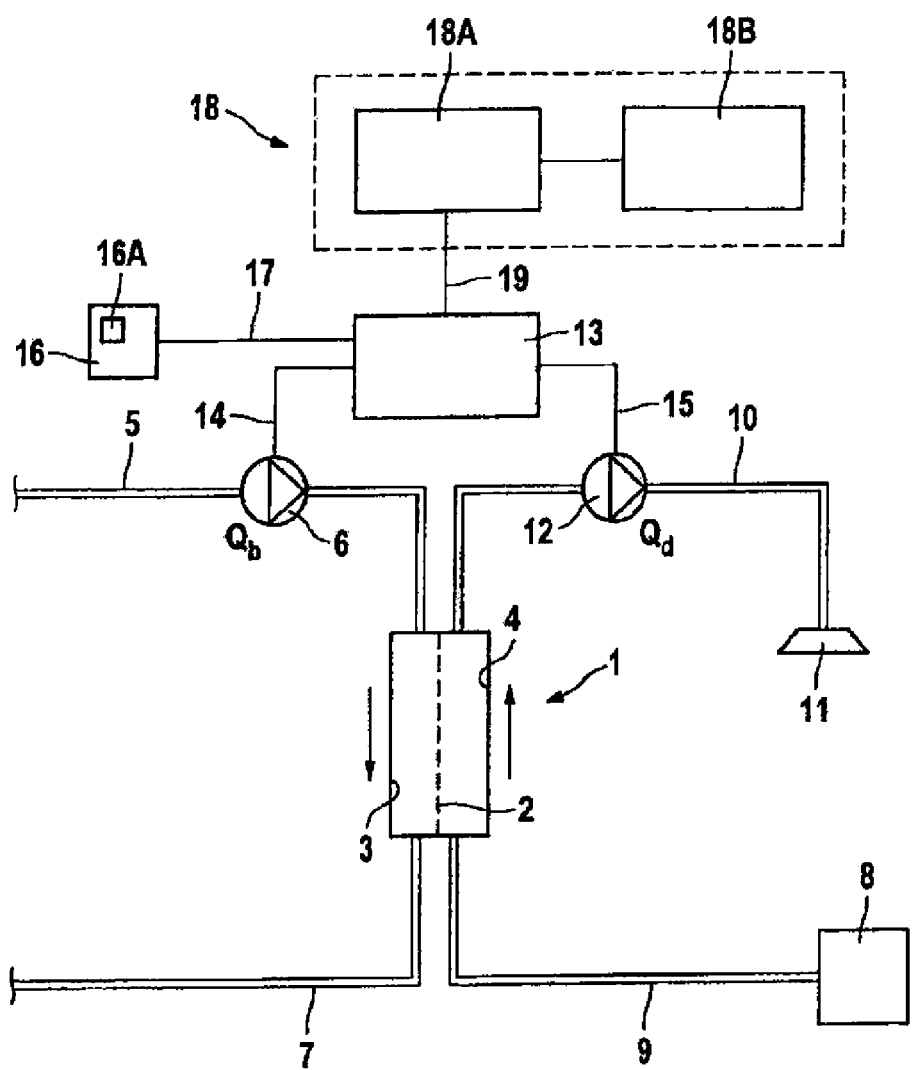
FIG. 1 is a highly simplified schematic view of the principal components of an apparatus according to the present invention for the extracorporeal treatment of blood, having a system according to the present invention for presetting an optimum dialysis-fluid flow rate.

FIG. 1 shows an embodiment of a blood-treating apparatus according to the present invention which has a system according to the present invention for presetting an optimum dialysis-fluid flow rate. A blood-treating apparatus which has a system according to the present invention for presetting an optimum blood flow rate differs from the apparatus shown in FIG. 1 only in that what is determined in accordance with the criteria according to the present invention is not the dialysis-fluid flow rate $Q_d$ as a function of the blood flow rate, but the blood flow rate $Q_b$ as a function of the dialysis-fluid flow rate $Q_d$, which, if it were increased by a given amount, would result in a metric characteristic of the effectiveness of the blood treatment increasing by not less than a given amount. Otherwise, both pieces of apparatus comprise the same components.

For greater clarity, it is only the essential components of the blood-treating apparatus which are shown in FIG. 1 because the individual components of a blood-treating apparatus for hemodialysis or hemodiafiltration will be generally familiar to the person skilled in the art.

The dialysis apparatus according to the present invention has a dialyser 1 which is divided by a semi-permeable membrane 2 into a blood chamber 3 and a dialysis-fluid chamber 4. From a patient, an arterial blood line 5, into which a blood pump 6 is connected, runs to an inlet of the blood chamber 3 of the dialyser, while a venous blood line 7 runs from an outlet of the blood chamber to the patient.

Fresh dialysis fluid is made available in a dialysis-fluid source 8. From the dialysis-fluid source 8, a dialysis-fluid inlet line 9 runs to an inlet of the dialysis-fluid chamber 4 of the dialyser 1, while a dialysis-fluid outlet line 10 runs from an outlet of the dialysis-fluid chamber to a discharge outlet 11. A dialysis-fluid pump 12 is connected into the dialysis-fluid outlet line 10.

The dialysis apparatus has a control unit 13 which is connected to the blood pump 6 and the dialysis-fluid pump 12 via control lines 14, 15, respectively. The control unit 13 produces control signals for operating the blood and dialysis-fluid pumps 6, 12 at a preset pumping rate so that a preset blood flow rate $Q_b$ is set in the blood line 5 and a preset dialysis-fluid flow rate $Q_d$ is set in the dialysis-fluid line.

For the input of various parameters for the dialysis, the dialysis apparatus has an input unit 16 which has for example an alphanumeric keyboard 16A. As well as various other variables, the blood flow rate $Q_b$ and a metric characteristic of the effectiveness of the dialyser 1 that is being used, and in particular the mass transfer coefficient k0A of the dialyser, may be entered with the input unit 16. Via a data line 17, the input unit 16 is connected to the control unit 13, by which the individual components of the dialysis apparatus, and in particular the blood and dialysis-fluid pumps, are operated in such a way that the dialysis treatment is performed with the preset dialysis parameters.

For a preset blood flow rate $Q_b$, the dialysis apparatus presets an optimum dialysis-fluid flow rate $Q_d$. For this purpose, the dialysis apparatus has an arrangement 18 for presetting the optimum dialysis-fluid flow rate $Q_{dopt}$, the construction and operation of which will be described in detail in what follows.

It is assumed that the dialysis treatment will be performed with a given dialyser 1 which has a given effectiveness which can be specified by means of the mass transfer coefficient k0A of the dialyser. In the case of hemodialysis, clearance K is calculated from the blood flow rate $Q_b$, the dialysis-fluid flow rate $Q_d$ and the mass transfer coefficient k0A of the dialyser 1 using the following equation:

$$K = Q_b \frac{e^{k0A\left(\frac{1}{Q_b}-\frac{1}{Q_d}\right)} - 1}{e^{k0A\left(\frac{1}{Q_b}-\frac{1}{Q_d}\right)} - \frac{Q_b}{Q_d}}$$ Equation (1)

Figure 2:
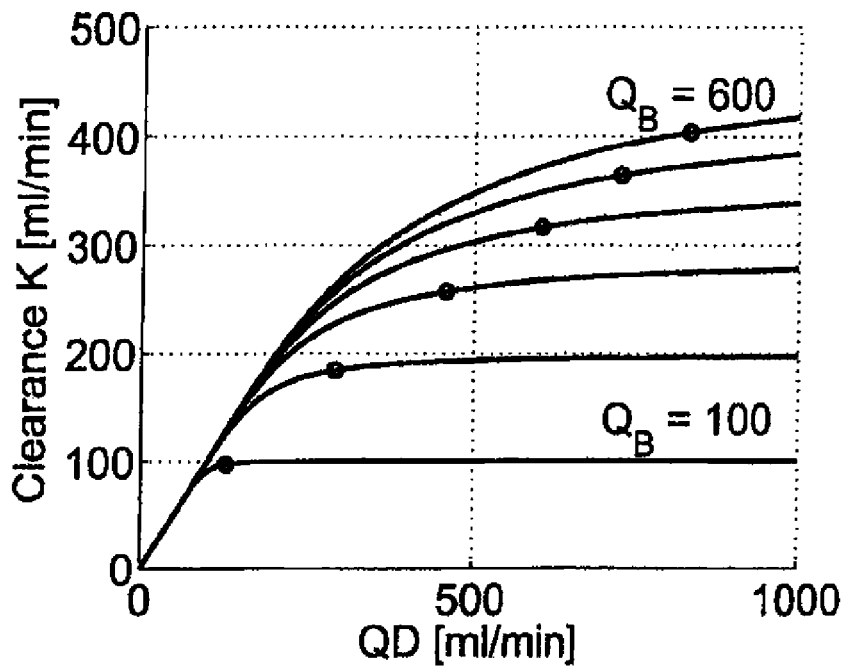
FIG. 2 shows clearance K (ml/min) as a function of the dialysis-fluid flow rate $Q_d$ (ml/min) for a given dialyser for various blood flow rates $Q_b$.
Figure 3:
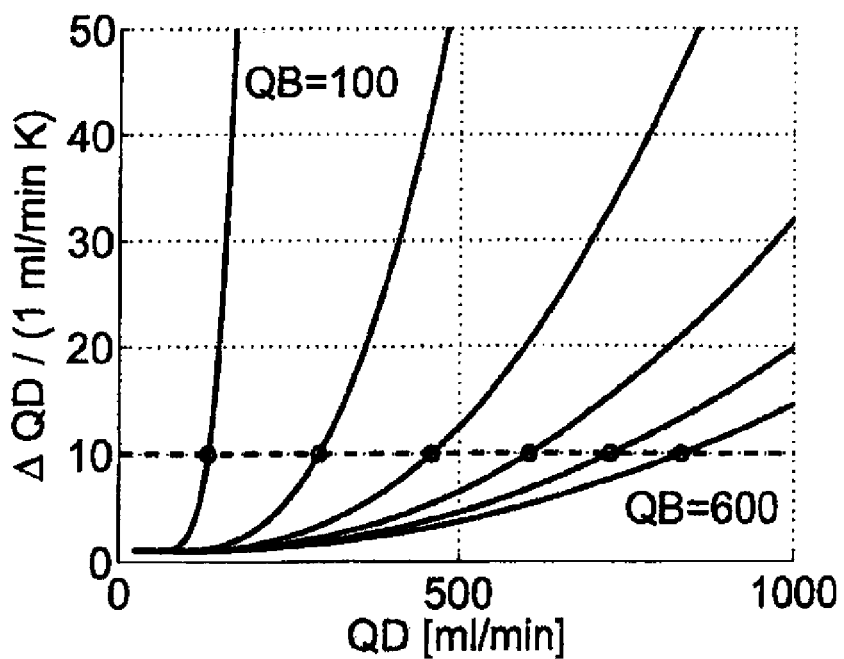
FIG. 3 shows the additional amount of dialysis fluid that is required to increase clearance by 1 ml/min at different dialysis-fluid flow rates $Q_d$ and blood flow rates $Q_b$.

FIG. 2 shows clearance K as a function of dialysis-fluid flow rate $Q_d$ for various blood flow rates $Q_b$. It can be seen that a saturation of clearance K occurs at high dialysis-fluid flow rates $Q_d$. Therefore, as from a certain blood flow rate, an increase in dialysis-fluid flow rate ceases to produce any appreciable gain in clearance. As a function of the blood flow rate $Q_b$, the system according to the present invention presets an optimum dialysis-fluid flow rate $Q_{dopt}$ as an optimum operating point for the dialysis apparatus. The optimum operating points for different blood flow rates are indicated in FIG. 2 by circles, a ratio of additional dialysis fluid per ml/min of additional clearance of 10:1 having been selected for the operating points. If, starting from the given operating point, a further increase is made in the dialysis-fluid flow rate $Q_d$, then an increase in the dialysis-fluid flow rate no longer involves an increase of more than a given amount in a metric characteristic of the dialysis treatment, and in particular in the clearance K. Hence, the optimum dialysis-fluid flow rate $Q_{dopt}$ is that dialysis-fluid flow rate which, when exceeded, results in the derivative of the function shown in FIG. 1, which defines the dependence on the dialysis-fluid flow rate $Q_d$ of the metric characteristic of the dialysis treatment, in particular the clearance K, being less than a given value. Consequently, what is considered is not the absolute value of clearance but the derivative. FIG. 3 shows how many ml/min of additional dialysis-fluid are required at different blood flow rates $Q_b$ from 100 ml/min to 600 ml/min to increase the clearance K by 1 ml/min.

Trials have shown that in practice a ratio of 10:1 gives an operating point at which relatively high effectiveness is obtained from the dialysis treatment for an acceptable consumption of dialysis fluid. This target criterion of 10:1 is indicated in FIG. 3 by a horizontal dashed line. The respective intersections with the curves for the different blood flow rates represent the various operating points. Because the derivative of the dialysis-fluid-flow-rate-dependent function described above cannot readily be actually calculated, the present invention makes provision for iterative approximate solutions.

In FIGS. 2 and 3, it can clearly be seen that at a blood flow rate $Q_b$=100 ml/min the operating point is in the saturation range. However, at the operating point for $Q_b$=600 ml/min it could be assumed that a further increase in the dialysis-fluid flow rate would still give a pertinent gain in clearance. However, an objection that has to be raised in this case is that, to the right of the operating point, the dialysis-fluid flow rate would have to be raised by more than 10 ml/min to obtain a gain in clearance of only 1 ml/min.

Figure 4:
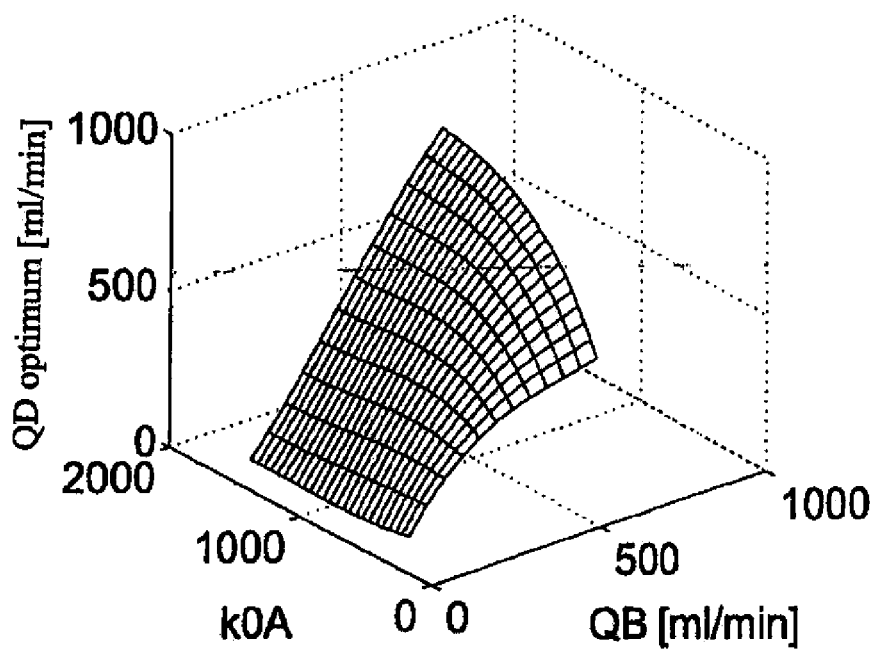
FIG. 4 shows a three-dimensional family of characteristics in which the optimum dialysis-fluid flow rate $Q_{dopt}$ is represented as a function of blood flow rate $Q_b$ and the mass transfer coefficient of the dialyser.

FIGS. 2 and 3 show clearance as a function of dialysis-fluid flow rate only for one specific type of dialyser which has a given mass transfer coefficient k0A. However, in practice different dialysers which differ in having different mass transfer coefficients can be used in pieces of dialysis apparatus. FIG. 4 shows a three-dimensional family of characteristics from which the optimum dialysis-fluid flow rate $Q_{dopt}$ can be determined as a function of the blood flow rate $Q_b$ for different dialysers, which are each distinguished by a given mass transfer coefficient k0A.

The family of characteristics shown in FIG. 4 could be stored in the form of a table in a memory of the arrangement 18 according to the present invention for presetting the optimum dialysis-fluid flow rate. However, for reasons of storage space, the present invention makes provision for the family of characteristics to be approximated by means of a suitable function. Various mathematical processes are known for this purpose.

In the embodiment described, the three-dimensional family of characteristics is approximated by a third-order polynomial in two axes using all the possible cross-terms. This gives the following modelling equation having 4×4=16 parameters a(i,j):

$$QD_{opt} = a_{33} \cdot Q_b^3 k_{0A}^3 + a_{32} \cdot Q_b^3 k_{0A}^2 \ldots a_{30} \cdot Q_b^3 k_{0A}^0$$

$$+ a_{23} \cdot Q_b^2 k_{0A}^3 + a_{22} \cdot Q_b^2 k_{0A}^2 \ldots a_{20} \cdot Q_b^2 k_{0A}^0$$

$$\ldots$$

$$+ a_{03} \cdot Q_b^0 k_{0A}^3 + a_{02} \cdot Q_b^0 k_{0A}^2 \ldots a_{00} \qquad \text{Equation (2)}$$

The individual parameters in the above system of equations are determined by the least squares method, thus minimizing the sum of the squared differences between the raw data and the model. In practice, the match between the family of characteristics (surface) and the modelling equation is sufficiently good.

For the dialysis treatment to be performed, the treating physician presets a given blood flow rate $Q_b$, which he enters from the keyboard 16A of the input unit 16, whereupon the control unit 13 sets the pumping rate (speed) of the blood pump 6 accordingly. From the input unit 16, the physician also enters details of which dialyser 1 is being used for the dialysis treatment, whereupon the mass transfer coefficient k0A belonging to the given type of dialyser, which is stored in a memory, is determined. It is however also possible for the particular mass transfer coefficient k0A of the dialyser that is being used to be entered directly.

The values of the preset blood flow rate $Q_b$ and the preset mass transfer coefficient k0A are received from the control unit 13 by the arrangement 18 via a data line 19. The arrangement 18 has a calculating unit 18A which calculates the optimum dialysis-fluid flow rate $Q_{dopt}$ on the basis of the third-order equation described above. To show the optimum dialysis-fluid flow rate $Q_{dopt}$, the arrangement 18 has an indicating unit 18B, in the form of a screen or display for example.

The arrangement 18 also transmits the value calculated for the optimum dialysis-fluid flow rate $Q_{dopt}$ via the data line 19 to the control unit 16, which in turn sets the speed of the dialysis-fluid pump 12 in such a way that the dialysis fluid is pumped at the optimum dialysis-fluid flow rate $Q_{dopt}$.

In a preferred embodiment, the input unit 16 makes provision for the input of different target criteria. What may be set as a target criterion in addition to the ratio of 10:1 described above is for example a ratio of 5:1, i.e. 5 ml/min of additional dialysis fluid for 1 ml/min of additional clearance and a ratio of 15:1 or 20:1.

As a function of the mode set (5:1, 10:1 and 15:1 or 20:1), the calculating unit 18A of the arrangement 18 then calculates the optimum dialysis-fluid flow rate $Q_{dopt}$. The ratio of 5:1 represents in this case an economical mode in which, although dialysis fluid is to be saved, the accustomed clearance cannot be achieved, the ratio of 10:1 represents a normal mode and the ratio of 15:1 or 20:1 represents an intensive mode in which particularly high clearance is to be achieved but by using a larger amount of dialysis fluid.

In the event of allowance also being made for the ultrafiltrate flow in hemodialysis, what is obtained in place of equation (1) given above is the following equation (1') for hemodialysis with allowance made for the ultrafiltration:

$$K = \frac{1 - \exp\left[\frac{k_0 A}{Q_B} \cdot \left(1 - \frac{Q_B}{Q_D}\right)\right]}{\frac{Q_B}{Q_D} - \exp\left[\frac{k_0 A}{Q_B} \cdot \left(1 - \frac{Q_B}{Q_D}\right)\right]} \cdot Q_B \cdot \left(1 - \frac{Q_F}{Q_B}\right) + Q_F \qquad \text{Equation (1')}$$

where
$Q_B$=blood flow
$Q_D$=dialysate flow
$Q_F$=filtrate flow, only ultrafiltration in the present case
k0A=mass transfer area coefficient.

In what follows, the more general case of hemodiafiltration will be described, in which not only hemodialysis but also hemofiltration takes place. In the case of hemodiafiltration, the relationship between the flow rates is defined by the following more general equation (1″) for hemodiafiltration.

$$K = Q_{Bi} \cdot \frac{1 - \frac{Q_{Do}}{Q_{Di}} \cdot \frac{Q_{Bo}}{Q_{Bi}} Z}{1 - \frac{Q_{Bo}}{Q_{Di}} Z} \qquad \text{Equation (1″)}$$

where $$Z = \left(1 - \frac{Q_F}{Q_{Bi}}\right)^{\frac{p}{Q_F} - 1} \cdot \left(1 - \frac{Q_F}{Q_{Do}}\right)^{-\left(\frac{p}{Q_F} - 1\right)}$$

$$p = k_0 A + (1 - \sigma) \cdot (1 - f) \cdot Q_F$$

$$f = \frac{1}{Pe} - \frac{1}{\exp(Pe) - 1}$$

$$Pe = (1 - \sigma) \cdot \frac{Q_F}{k_0 A}$$

where
σ=reflection coefficient (0<σ<1), e.g. σ=0 for urea
i=subscript for inflow
o=subscript for outflow
$Q_F$=total filtration rate=sum of ultrafiltration rate $Q_{UF}$ and substitution rate $Q_S$ $$Q_F = Q_{UF} + Q_S$$

$Q_{Di}$=flow which is present at the dialysate inlet of the dialyser; generally corresponds to the dialysate flow $Q_D$ set on the machine
$Q_{Do}$=flow which is present at the dialysate outlet of the dialyser $$Q_{Do} = Q_{Di} + Q_F$$

$Q_{Bi}$=flow which is present at the blood inlet of the dialyser $$Q_{Bi} = Q_B + f \cdot Q_S$$

where f is a factor for pre-dilution or post-dilution; f=0 for post-dilution, f=1 for pre-dilution and f=between 0 and 1 for mixed dilution
$Q_{Bo}$=flow which is present at the blood outlet of the dialyser $$Q_{Bo} = Q_{Bi} + Q_F$$

$Q_B$=blood flow which is present in the extra-corporeal blood circuit upstream of the point of arterial infusion; generally corresponds to the blood flow set by the user.

Figure 5:
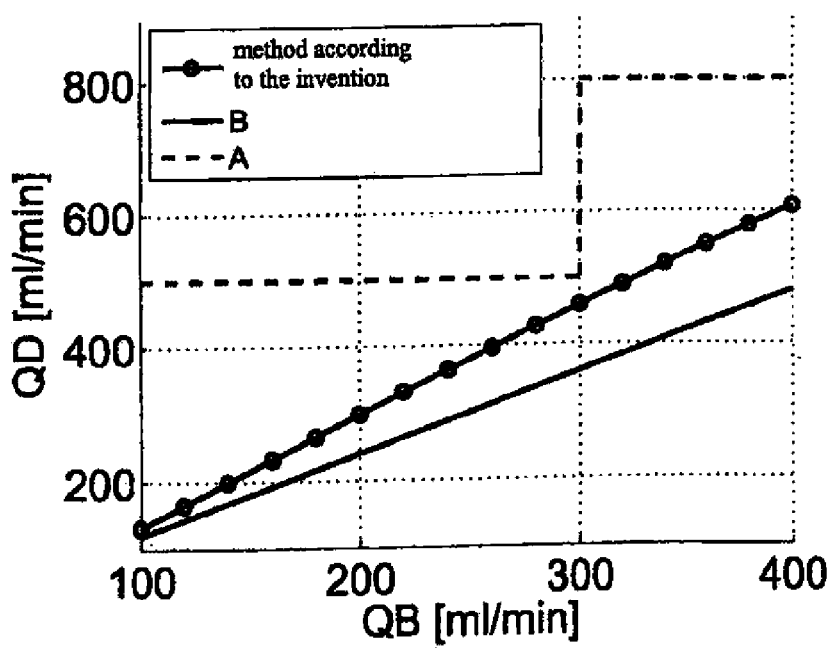
FIG. 5 shows dialysis-fluid flow rate $Q_d$ (ml/min) as a function of blood flow rate $Q_b$ (ml/min) in the case of the method according to the present invention, i.e. the system according to the present invention, in comparison with known methods.
Figure 6:
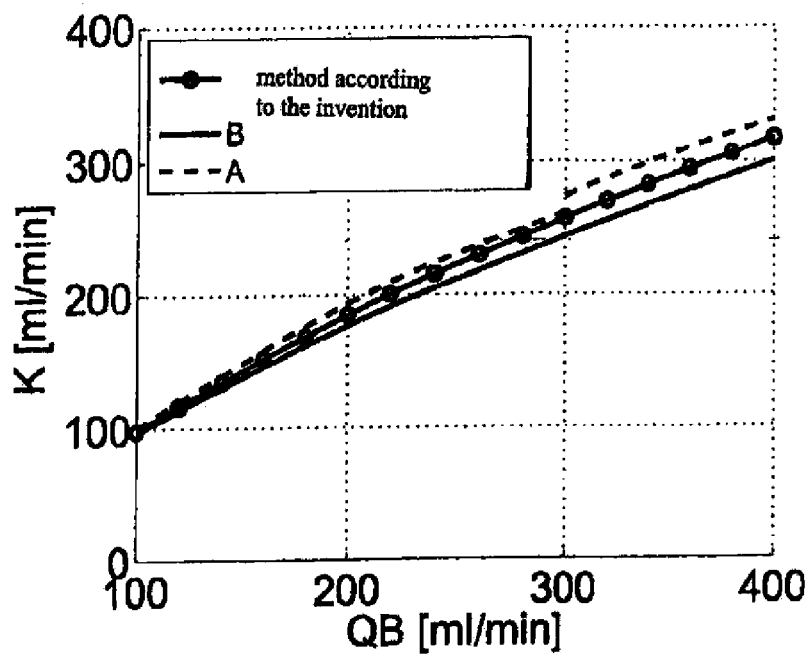
FIG. 6 shows clearance K (ml/min) as a function of blood flow rate $Q_b$ (ml/min) in the case of the method according to the present invention, or in other words the system according to the present invention, in comparison with known methods.

The differences of the method according to the present invention for presetting a given dialysis-fluid flow rate as compared with the known methods will be described below by reference to FIGS. 5 to 9. In FIGS. 5 to 9, a known method in which a constant dialysis-fluid flow rate $Q_d$ of 500 ml/min is set for blood flow rates $Q_b$ Up to 300 ml/min and a constant dialysis-fluid flow rate $Q_d$ of 800 ml/min is set for blood flow rates $Q_b$ greater than 300 ml/min is shown as "A." A known method in which the dialysis-fluid flow rate is calculated by multiplying the blood flow rate $Q_b$ by a factor of 1.2 is shown as "B." FIG. 5 shows dialysis-fluid flow rate $Q_d$ as a function of blood flow rate $Q_b$ for the method according to the present invention as compared with the known methods "A" and "B,"

while FIG. 6 shows clearance K as a function of blood flow rate for the method according to the present invention and the known methods "A" and "B."

Figure 7:
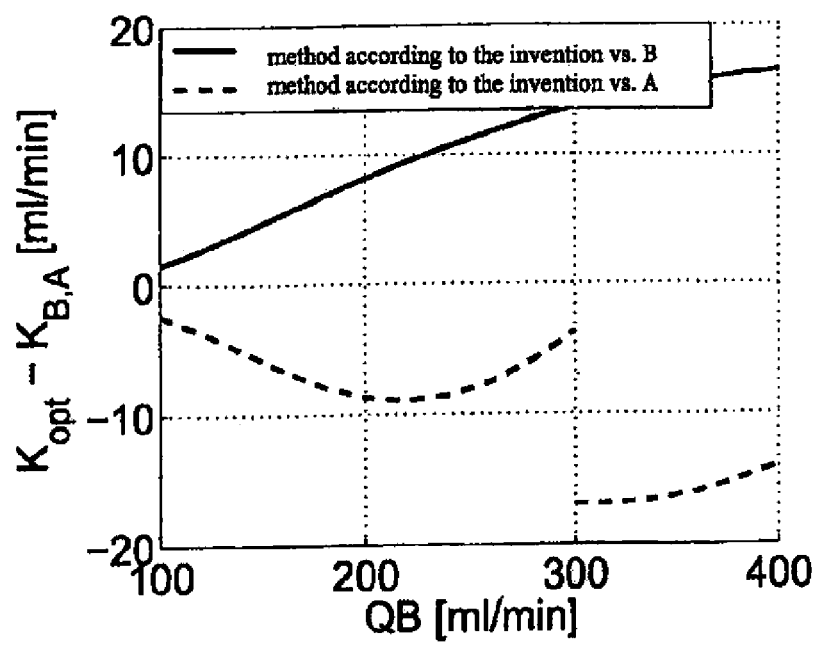
FIG. 7 shows the difference between clearance $K_{opt}$ in the case of the method according to the present invention, or in other words the system according to the present invention, and clearance K(A, B) in the case of known methods, as a function of the blood flow rate $Q_b$ (ml/min).

FIG. 7 shows, as a function of the blood flow rate $Q_b$, the difference between the clearance $K_{opt}$ at the optimum dialysis-fluid flow rate $Q_{dopt}$ achieved with the method according to the present invention and the clearances $K_A$ and $K_B$ achieved with the known methods, to give a clearer picture of the differences between the method according to the present invention and the known methods with regard to the change in clearance. Compared with the known method "A," a relatively large amount of dialysis fluid is saved with the method according to the present invention, even though clearance is reduced by only a relatively small amount. It is true that with method "B" more dialysis fluid is saved than with method "A," but it also results in a larger reduction in clearance.

Figure 8:
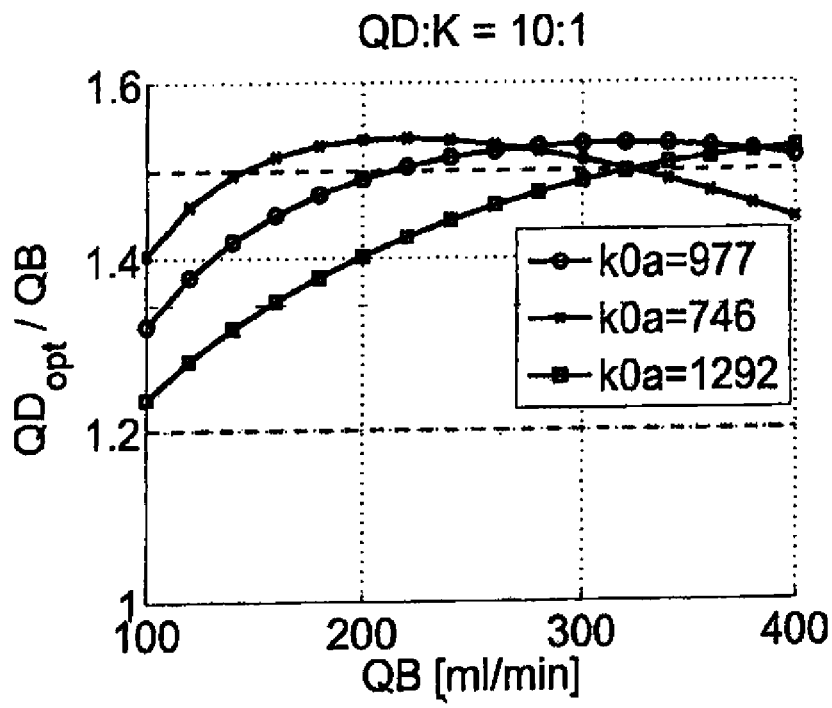
FIG. 8 shows the quotient of optimum dialysis-fluid flow rate $Q_{dopt}$ divided by blood flow rate $Q_b$ in accordance with the present invention as a function of blood flow rate $Q_b$, in comparison with the known methods.
Figure 9:
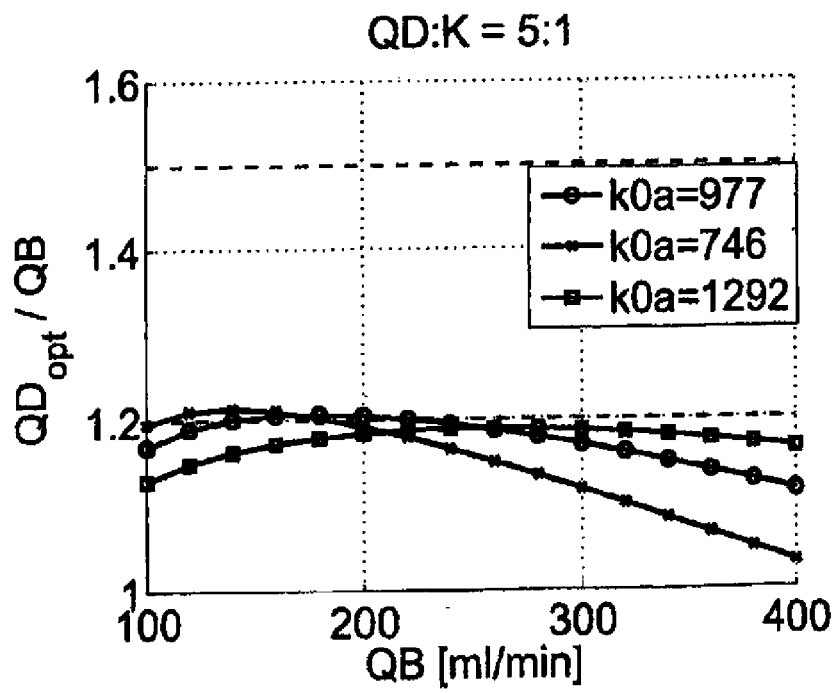
FIG. 9 shows the quotient of optimum dialysis-fluid flow rate $Q_{dopt}$ divided by blood flow rate $Q_b$ as a function of blood flow rate $Q_b$, in comparison with known methods.

For the selected "target criteria" of 10:1 (FIG. 8) and 5:1 (FIG. 9), FIGS. 8 and 9 show the optimum dialysis-fluid flow rates $Q_{dopt}$ that are standardised in accordance with the present invention to the blood flow rate, for three different dialysers. It can be seen that, for the selected target criterion of 10:1, a factor of 1.5 is only plausible for different dialysers as a first approximation in the working range between $Q_b$=200 and 400. The factor of 1.2 on the other hand is too low for the target criterion of 10:1. The position changes however if a target criterion of 5:1, i.e. 5 ml/min of dialysis fluid for 1 ml/min of clearance, is selected. It can be seen that a factor of 1.2 is a better approximation in this case. With the teaching according to the present invention, a compromise is successfully found between methods A and B, the user being given at the same time quantified operating points at which he has a direct overview of the effects which increases in flow rate have on the effectiveness of the treatment.

The invention claimed is:

1. A system for pre-setting a flow rate for an extracorporeal blood-treating apparatus comprising a dialyser divided into a blood chamber and a dialysis chamber by a semi-permeable membrane, wherein blood flows through the blood chamber and dialysis fluid flows through the dialysis chamber, said system comprising
a means for selecting an optimum flow rate, said means for selecting an optimum flow rate being selected from the group consisting of:
a means for selecting an optimum dialysis fluid flow rate $Q_{dopt}$ as a function of a pre-set blood flow rate $Q_b$, wherein $Q_{dopt}$ for the pre-set blood flow rate $Q_b$ is a solution for $Q_{dopt}$ such that if $Q_{dopt}$ were increased by a first given amount, a metric characteristic of the effectiveness of the blood treatment would increase by approximately a second given amount; and
a means for selecting an optimum blood flow rate $Q_{dopt}$ as a function of a pre-set dialysis fluid flow rate $Q_d$, wherein $Q_{bopt}$ for the pre-set dialysis fluid flow rate $Q_d$ is a solution for $Q_{bopt}$ such that if $Q_{bopt}$ were increased by a third given amount, a metric characteristic of the effectiveness of the blood treatment would increase by approximately a fourth given amount,
wherein the means for selecting $Q_{dopt}$ or the means for selecting $Q_{bopt}$ is a calculating unit configured such that $Q_{dopt}$ or $Q_{bopt}$ is calculated from a mathematical equation by an iterative approximate solution method.

2. The system of claim 1, wherein the metric characteristic of the effectiveness is a clearance K of the dialysis treatment.

3. The system of claim 2, configured such that $Q_{bopt}$ or $Q_{dopt}$ is selected as a function of a metric characteristic of the dialyser.

4. The system of claim 1, configured such that $Q_{bopt}$ or $Q_{dopt}$ is selected as a function of a metric characteristic of the dialyser.

5. The system of claim 4, wherein the metric characteristic of the dialyser is a mass transfer coefficient k0A of the dialyser.

6. The system of claim 5, further comprising
an input unit for presetting various modes of treatment in which the effectiveness of the blood treatment differs, configured such that for a first given mode of treatment and a second given mode of treatment:
a ratio of the first given amount to the second given amount for the first given mode of treatment differs from a ratio of the first given amount to the second given amount for a second given mode of treatment; or
a ratio of the third given amount to the fourth given amount for the first given mode of treatment differs from a ratio of the third given amount to the fourth given amount for the second given mode of treatment.

7. The system of claim 1, further comprising:
an input unit for presetting various modes of treatment in which the effectiveness of the blood treatment differs, configured such that for a first given mode of treatment and a second given mode of treatment:
a ratio of the first given amount to the second given amount for the first given mode of treatment differs from a ratio of the first given amount to the second given amount for the second given mode of treatment; or
a ratio of the third given amount to the fourth given amount for the first given mode of treatment differs from a ratio of the third given amount to the fourth given amount for the second given mode of treatment.

8. The system of claim 1, wherein the mathematical equation is a multi-order polynomial.

9. A blood-treating apparatus for the extracorporeal treatment of blood, comprising:
a dialyser divided by a semi-permeable membrane into a blood chamber and a dialysis chamber, wherein blood flows through the blood chamber at a pre-set blood flow rate $Q_b$, or a dialysis fluid flows through the dialysis chamber a pre-set dialysis fluid rate $Q_d$; and
the system for pre-setting a flow rate of claim 1.

10. The blood-treating apparatus of claim 9, further comprising:
a control unit for pre-setting $Q_d$ or $Q_b$.

11. The blood-treating apparatus of claim 10, further comprising:
at least one of:
a dialysis-fluid pump for pumping the dialysis fluid, and
a blood pump for pumping blood,
wherein the control unit is configured to set the speed of the dialysis fluid pump at the pre-set dialysis flow rate $Q_d$ or to set the speed of the blood pump at the pre-set blood flow rate $Q_b$.

12. A method for pre-setting a dialysis fluid flow rate or a blood flow rate for an extracorporeal blood-treating apparatus comprising a dialyser divided into a blood chamber and a dialysis chamber by a semi-permeable membrane, wherein the blood flows through the blood chamber and dialysis fluid flows through the dialysis chamber, the method comprising:
selecting an optimum dialysis fluid flow rate $Q_{dopt}$ as a function of a pre-set blood flow rate $Q_b$ at a pre-set blood flow rate $Q_b$ such that if $Q_{dopt}$ were increased by a first given amount, a metric characteristic of the effectiveness of the blood treatment would increase by approximately a second given amount; or selecting an optimum blood flow rate $Q_{bopt}$ as a function of a pre-set dialysis fluid flow rate $Q_d$ at a pre-set dialysis fluid flow rate $Q_d$ such that if $Q_{bopt}$ were increased by a third given amount, a metric characteristic of the effectiveness of the blood treatment would increase by approximately a fourth given amount, wherein $Q_{dopt}$ or $Q_{bopt}$ is calculated from a mathematical equation by an iterative approximate solution method.

13. The method of claim 12, wherein the metric characteristic of the effectiveness is a clearance K of the dialysis treatment.

14. The method of claim 12, further comprising selecting $Q_{bopt}$ or $Q_{dopt}$ as a function of a metric characteristic of the dialyser.

15. The method of claim 14, wherein the metric characteristic of the dialyser is a mass transfer coefficient k0A of the dialyser.

16. The method of claim 12, further comprising:
presetting at least two modes of treatment in which the effectiveness of the blood treatment differs, such that for a first given mode of treatment and a second given mode of treatment:
a ratio of the first given amount to the second given amount for the first given mode of treatment differs from a ratio of the first given amount to the second given amount for the second given mode of treatment; or
a ratio of the third given amount to the fourth given amount for the first given mode of treatment differs from a ratio of the third given amount to the fourth given amount for the second given mode of treatment.

17. The method of claim 12, wherein the mathematical equation is a multi-order polynomial.

18. A method comprising:
performing the method for pre-setting the dialysis fluid flow rate or the blood flow rate of claim 12; and
operating the extracorporeal blood-treating apparatus comprising a dialyser divided by a semi-permeable membrane into a blood chamber and a dialysis chamber, wherein blood flows through the blood chamber at the pre-set blood flow rate $Q_b$, or a dialysis fluid flows through the dialysis chamber at the pre-set dialysis fluid rate $Q_d$.

* * * * *

UNITED STATES PATENT AND TRADEMARK OFFICE
CERTIFICATE OF CORRECTION

PATENT NO. : 8,512,271 B2  Page 1 of 1
APPLICATION NO. : 12/443001
DATED : August 20, 2013
INVENTOR(S) : Moissl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1003 days.

Signed and Sealed this
Fifteenth Day of September, 2015

Michelle K. Lee
*Director of the United States Patent and Trademark Office*